United States Patent [19]

Seckinger et al.

[11] Patent Number: 5,403,817
[45] Date of Patent: Apr. 4, 1995

[54] ARYLAMINOCARBONYL COMPOUNDS

[75] Inventors: Karl Seckinger, Riegel; Fred Kuhnen, Weil, both of Germany

[73] Assignee: Sandoz Ltd., Basel, Switzerland

[21] Appl. No.: 13,555

[22] Filed: Feb. 5, 1993

Related U.S. Application Data

[63] Continuation of Ser. No. 734,670, Jul. 23, 1991, abandoned.

[30] Foreign Application Priority Data

Jul. 27, 1990 [GB] United Kingdom ................ 9016476

[51] Int. Cl.$^6$ ................ A01N 43/90; C07D 471/04
[52] U.S. Cl. ................ 504/246; 546/121
[58] Field of Search ................ 546/121; 504/246

[56] References Cited

U.S. PATENT DOCUMENTS 4,437,877  3/1984  Nagano ................ 71/90
5,039,334  8/1991  Schallner ................ 71/95

FOREIGN PATENT DOCUMENTS 364797  4/1990  European Pat. Off. .
370955  5/1990  European Pat. Off. .
384973  9/1990  European Pat. Off. .

OTHER PUBLICATIONS

Tetrahedron v. 27 n. 14 pp 3119–3127 (Jul 1971) Ben-I-shai et. al.

Primary Examiner—Marianne M. Cintins
Assistant Examiner—Phyllis G. Spivack
Attorney, Agent, or Firm—Lynn Marcus-Wyner; Allen E. Norris

[57] ABSTRACT

Novel arylaminocarbonyl compounds, intermediates therefore, and the use of said compounds for the control of weeds are disclosed.

14 Claims, No Drawings

ARYLAMINOCARBONYL COMPOUNDS

This is a continuation of Ser. No. 07/734,670, filed Jul. 23, 1991, now abandoned.

This invention relates to novel arylaminocarbonyl compounds, intermediates therefore, synthesis thereof, and the use of said compounds for the control of weeds.

More particularly, one aspect of this invention relates to a compound of the formula (I)

wherein
- $R_2$ is halo or hydrogen;
- $R_3$ is halo, cyano or $C_{1-4}$alkyl;
- $R_4$ is H; halo; $NO_2$; $NH_2$; CN; $C_{1-8}$alkyl optionally substituted by CN; $C_{2-8}$alkenyl optionally substituted by CN; $C_{2-5}$alkoxy carbonyl$C_{1-4}$alkyl, whereby the carbon atom of the alkyl group alpha to the alkoxycarbonyl group may be substituted with one more $C_{2-5}$alkoxycarbonyl group or a cyano group; $C_{2-5}$alkoxycarbonyl$C_{1-4}$alkoxy$C_{1-4}$alkyl; $C_{2-5}$alkoxycarbonyloxy: $C_{2-5}$alkoxycarbonyl-$C_{2-5}$alkenyloxy; $C_{2-5}$alkynyloxy; $C_{3-6}$cycloalkyloxy; $C_{2-5}$alkenyloxy optionally substituted by halogen; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkoxy; $O(C_{1-4}$alkylene$)_nR_7$; $S(C_{1-4}$alkylene$)_nR_7$; $OCH(SR_8)COOR_9$; $NR_{10}R_{11}$; $COOR_{12}$; $C(O)NR_{13}R_{13}'$; $C(O)R_{14}$; or $R_{15}$;
- or $R_3$ and $R_4$ join together with the phenyl ring to form a bicyclic ring containing nine to ten ring atoms, one to three of said ring atoms optionally being selected from oxygen, nitrogen and sulfur, and optionally being substituted with one or more groups selected from $C_{2-8}$ alkynyl, halo, oxo, $C_{1-4}$alkylene-$R_{16}$, $C_{2-8}$alkenyl and $C_{1-8}$alkyl which is itself optionally substituted by $C_{2-5}$alkoxycarbonyl, $C_{1-4}$alkoxy or CN;
- $R_5$ is hydrogen; $C_{1-4}$alkyl; halogen; or $C_{2-4}$alkenyl;
- $R_6$ is COOH; COOW; COOSW; COON=CWW'; CONHSO$_2$W; CONHOCH$_2$COOW; COOCH$_2$OCOW; COOCHWOCOW'; or CONHOCH$_2$COOH;
- A is NH; or
- A and $R_6$ join together to form N—C(X) so oriented such that N is tied to the C=O moiety of formula (I);
- $R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by O—$C_{1-4}$alkylene-COOR$_8$; $C_{2-5}$alkanoyl; $C_{2-5}$alkoxycarbonyl wherein the alkoxy is optionally substituted by $C_{1-4}$alkylthio; $C(O)NR_8R_8'$; $C(=NOR_8)COOR_8'$; $P(O)(OR_8)OR_8'$; $R_{15}$; $C(O)R_{15}$; or cyclopentoxycarbonyl;
- $R_8$ and $R_8'$ independently are $C_{1-4}$alkyl;
- $R_9$ is $C_{1-4}$alkyl optionally substituted by one or more halo;
- $R_{10}$ is H or $C_{1-4}$alkyl;
- $R_{11}$ is H; $C_{1-4}$alkyl, optionally substituted by $P(O)(OR_8)R_8'$; $C_{2-5}$alkanoyl; $C_{2-5}$alkoxycarbonyl; or $C_{2-5}$alkoxycarbonyl$C_{1-4}$-alkyl;
- $R_{12}$ is $N=C_{2-8}$alkylidene; or $C_{1-4}$alkyl optionally substituted by one or more groups selected from halo, $C_{1-4}$alkoxy, tri($C_{1-4}$alkyl)silyloxy, tri($C_{1-4}$alkyl)silyl, $C_{2-5}$alkoxycarbonyl, $P(O)(OR_8)OR_8'$, $C_{2-5}$alkanoyloxy, and di($C_{1-4}$alkyl)aminocarbonyloxy in which both alkyl groups together with N may form a saturated 5 to 6 membered heteroring optionally containing one further heteroatom selected from O, S and N, and in which any further N-heteroatom present may,
- depending on the hydrogenation degree of the heteroring, bear a
- hydrogen or a $C_{1-4}$alkyl group;
- $R_{13}$ is H or $C_{1-4}$alkyl; and
- $R_{13}'$ is H, $C_{1-4}$alkyl, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy;
- or $R_{13}$ and $R_{13}'$ together with N form a 5 to 6 membered heteroring optionally containing one or two further heteroatoms selected from O, S and N, whereby, depending on the hydrogenation degree of the heteroring, any further N-heteroatom may bear hydrogen or be substituted by $C_{1-4}$alkyl;
- $R_{14}$ is H or $C_{1-4}$alkyl;
- $R_{15}$ is a heterocyclic ring having 5 or 6 ring atoms, one to three of said ring atom being selected from oxygen, sulfur and nitrogen, which ring is optionally substituted with one or more groups selected from $C_{1-4}$alkyl and $C_{2-5}$alkoxycarbonyl;
- $R_{16}$ is tetrahydropyranyl, 5,6-dihydro-2H-thiinyl, pyridyl, pyrazinyl, oxazolyl, or oxadiazolyl all of which are optionally substituted with $C_{1-4}$alkyl;
- W and W' are independently $C_{1-8}$alkyl, $C_{2-8}$alkenyl, $C_{2-8}$alkynyl, or phenyl, each of which is optionally substituted by CN, $C_{1-4}$alkoxy or one or more halo;
- n is 0 or 1; and
- m is 0 to 4.

Compounds of the formula (I) wherein A and $R_6$ join together to form N—C(X) are hereinafter referred to as hydantoins. Compounds of the formula (I) wherein A and $R_6$ do not join together are hereinafter referred to as ureas.

Any alkyl group in the compound of formula (I) may be branched or straight chain and preferably has one to four backbone carbon atoms.

Any alkenyl or alkynyl group may be either branched or straight chain and preferably has three to five backbone carbon atoms.

Any cycloalkenyl group preferably has five to six carbon ring atoms.

Any cycloalkyl group preferably has three to five carbon ring atoms.

When the compound of formula I is substituted by halogen, it is preferably chlorine or fluorine, more preferably fluorine.

Where $R_3$ and $R_4$ join together with the phenyl ring to form a bicyclic ring, it is preferably an indanone; a benzazinone, particularly a quinolinone; a benzoxazinone; a benzodiazinone, particularly dihydroquinoxalinone; a benzothiazinone; a benzodioxane; a benzopyrane; a benzopyrone, particularly coumarin; a benzazole, particularly an indole, an indolone, an indazole, a benzotriazole, an isatine or a benzimidazolone; a benzoxazolone; a benzothiazolone; a benzofurane; or a benzdioxolane.

Where m is 2–4, each $R_4$ substituent may be the same or different.

Preferred substituents in such cases where the compound of formula (I) is a hydantoin compound are the following:

A is N—C(O);
$R_2$ is Cl or F;
$R_3$ is Cl or CN;
$R_4$ is hydrogen; $C_{1-5}$alkoxy optionally substituted by CN; OH; $C_{1-4}$alkoxycarbonyl$C_{1-4}$alkoxy; halogen; CN; $C_{1-4}$alkylsulfonyloxy; $C_{2-5}$alkynyloxy; $C_{3-6}$cycloalkyloxy $C_{2-5}$alkoxycarbonyloxy; $C_{2-5}$alkenyloxy optionally substituted by halogen; $C_{2-5}$alkoxycarbonyl; $C_{2-5}$alkenyloxy; $C_{1-4}$alkylsulfonyl; $NO_2$; $C_{1-4}$alkylthio, $C_{2-5}$alkoxycarbonyl; or
$R_3$ and $R_4$ join together with the phenyl ring to form 5-F-indan-1-on-6-yl or 4-($C_2H_5OCOCH_2$)-7-F-2,4-dihydro-benzo[b]-1,4-oxazin-3-on-6yl; and
$R_5$ is H or halogen.

Especially preferred substituents in such cases where the compound of formula (I) is a hydantoin compound are the following:

A is N—(CO);
$R_2$ is F;
$R_3$ is Cl;
$R_4$ is $C_{1-4}$alkoxy, $C_{2-5}$alkynyloxy, $C_{2-5}$alkenyloxy or $C_{2-5}$alkoxycarbonyl; and
$R_5$ is H or F.

Preferred substituents in such cases where the compound of formula (I) is a urea compound are the following:

$R_2$ is F;
$R_3$ is Cl;
$R_4$ is $C_{1-4}$alkoxy, $C_{2-5}$alkoxycarbonyl, $C_{2-5}$alkoxycarbonyloxy, $C_{1-4}$alkylsulfonyloxy, hydrogen, halogen, cyano, $C_{2-5}$alkynyloxy, $C_{3-6}$cycloalkyloxy, $NO_2$ or $C_{1-5}$alkylthio; or
$R_3$ and $R_4$ join together with the phenyl ring to form 5-F-indan-1-on-6-yl or 4-($C_2H_5OCOCH_2$)-7-F-2,4-dihydro-benzo[b]-1,4-oxazin-3-on-6-yl;
$R_5$ is hydrogen or halogen; and
$R_6$ is $C_{2-8}$alkoxycarbonyl.

Especially preferred substituents in such cases where the compound of formula (I) is a urea compound are the following:

$R_2$ is F;
$R_3$ is Cl;
$R_4$ is $C_{2-5}$alkoxy or $C_{1-4}$alkynyloxy; and
$R_5$ is hydrogen or F;
$R_6$ is $C_{2-5}$alkoxycarbonyl.

Urea compounds of the formula (I) may be prepared by reacting a compound of the formula (II)

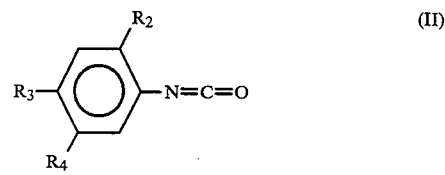

wherein $R_{2-4}$ are as previously defined, with a compound of the formula (III)

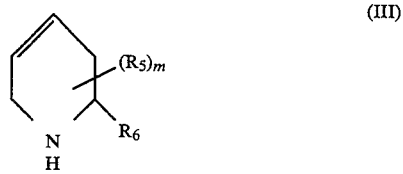

wherein $R_{5-6}$ and m are as previously defined.

This reaction can be carried out in various solvents under various conditions. In one embodiment, the reaction is carried out in the presence of a base in an aqueous solution. Preferred bases are the alkali metal hydroxides such as sodium hydroxide or potassium hydroxide. This reaction is carried out at reduced temperatures, i.e. at a temperature below room temperature, preferably from about 0°–20° C. The desired end-product can be worked-up by known techniques, for example, acidification, filtration, and extraction.

In a second embodiment, the reaction is carried out in an inert solvent such as toluene, diethylether or methylene chloride at a temperature ranging from 0°–100° C., preferably at or near ambient temperature. The desired end-product is, again, worked-up by known techniques, for example, by evaporation of solvent, chromatography and extraction.

Compounds of the formulae (II) and (III) are known and can be prepared by known procedures.

Hydantoin compounds of the formula (I) can be obtained from urea compounds of the formula (I) in such cases where X is oxygen. This reaction occurs through the condensation reaction between the amide and the ester group of the urea compound of formula (I) and is facilitated by the presence of an acid or a nucleophilic agent. In one embodiment, the reaction is carried out in an alcohol medium such as ethanol in the presence of an acid such as HCl. Suitable temperatures range from about room to reflux temperature, although the reaction is preferably carried out under reflux. The desired end-product is worked-up by known techniques, for example, evaporation and crystallization.

In a second embodiment, the reaction is carried out in an alcohol medium such as methanol in the presence of a nucleophilic agent such as $K_2CO_3$. Suitable temperatures range from about room temperature to 60°, preferably at about 50°. The resulting product is treated with ammonium chloride to yield the end-product, which can be worked-up from solution by known techniques such as extraction and crystallization.

Alternatively, the hydantoin compound of formula (I) can be generally obtained, i.e., with X being either oxygen or sulfur, by reacting a compound of the formula (IIa)

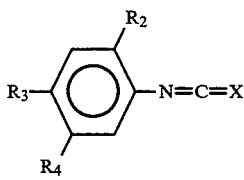

wherein $R_{2-4}$ being as previously defined and X being O or S with a compound of the formula (IIIa)

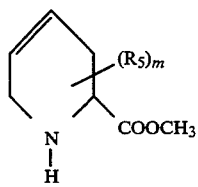

wherein $R_5$ and m are as previously defined.

This condensation reaction is preferably carried out in an inert solvent such as toluene. Condensation is facilitated by the presence of a nucleophilic agent such as a tertiary amine, e.g., a tri(alkyl)amine such as tri(ethyl)amine. Suitable reaction temperatures range from room to reflux temperature, and preferably is at or near ambient temperature. The desired end-product is, again, worked-up by known techniques, for example, by evaporation of solvent, filtration and crystallization.

Compounds of the formulae (IIa) and (IIIa) are known and can be prepared according to known procedures. The compounds of formula (I) are useful because they are effective in controlling the growth of plants. By plants it is meant germinating seeds, merging seedlings and established vegetation including underground portions. In particular, the compounds are useful as herbicides as indicated by causing damage to both monocotyledoneous and dtcotyledoneous plants in various standard evaluations for determining such effects. The herbicidal effects are exhibited both pre- and post-emergence the plants. Such herbicidal effects indicate that the compounds of formula (I) are particularly of interest in combatting weeds (unwanted plants).

The compounds of the formula (I) are indicated mainly to be stronger acting against dtcotyledoneous plants than monocotyledoneous plants. Relatively less toxicity towards crops than towards weeds is further indicated. Hence, the compounds are of particular interest as selective herbicides to combat weeds in a crop locus, particularly as locus of a crop such as, for example, sugarbeet, sunflower, cotton soybean, corn and wheat.

The present invention therefore also provides a method of combatting weeds in a locus which comprises applying to the weeds or their locus a herbicidally effective amount of a compound of the invention. When selective action is desired in crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.01 to 5 kg/hectare, more usually 0.01 to 1 kg/hectare, and preferably 0.01 to 0.5 kg/hectare, the application being repeated as necessary. When used in crops, the application usually will not exceed about 1 kg/hectare, and is usually in the range of 0.01 to 1 kg/hectare.

For practical use as herbicides, the compounds of formula (I) may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions of formulations may contain 0.01% to 99% by weight of active ingredient, from 0 to 20% by weight of agriculturally acceptable surfactants and 1 to 99.99% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as talc, clay, silica and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in micro-encapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifiability, spreading, wetting, dispersibility or other surface-modifying properties. Examples of surfactants are sodium lignin sulphonate and lauryl sulphate.

Carriers as used herein mean a liquid or solid material used to dilute a concentrated material to a usable or desirable strength. For dusts or granules it can be e.g.

talc, kaolin or diatomaceous earth, for liquid concentrate forms, a hydrocarbon such as xylene or an alcohol such as isopropanol; and for liquid application forms, e.g. water or diesel oil.

The compositions of this application can also comprise other compounds having biological activity, e.g. compounds having similar or complementary herbicidal activity or compounds having antidotal, fungicidal or insecticidal activity.

Typical herbicidal composition, according to this invention, are illustrated by the following examples A, B and C in which the quantities are in parts by weight.

EXAMPLE A

Preparation of a Dust

10 Parts of a compound of formula (I) and 90 parts of powdered talc are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder

25 Parts of a compound of formula (I) are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13 Parts of a compound of formula (I) are mixed in a beaker with 7 parts of Toximul 360A (a mixture of anionic and non-ionic surfactants containing largely non-ionic surfactants), 24 parts of dimethylformamide and 56 parts of Tenneco 500–100 (predominantly a mixture of alkylated aromatics such as xylene and ethylbenzene) until solution is effected. The resulting EC is diluted with water for use.

FINAL COMPOUNDS

Unless otherwise indicated, temperatures herein stated are in Celsius.

Example A

1[[(4-chloro-2-fluoro-5-isopropoxyphenyl)amino]carbonyl]1,2,3,6-tetrahydro-2-pyridinecarboxylic acid (Compound 1.1)

4,6 g (0,02 moles) of solid, finely powdered 4-chloro-2-fluoro-5-isopropoxyphenyl isocyanate are added in several portions with stirring to a solution of 3,28 g (0,02 moles) of 1,2,3,6-tetrahydro-2-pyridinecarboxylic acid hydrochloride in 40 ml of 1N NaOH solution. The temperature is maintained at 5° by means of an ice bath during the addition. When the addition is complete, the reaction solution is stirred at room temperature for a period of 4,5 hours and is then filtered by suction.

The filtrate is cautiously acidified with 15 percent hydrochloric acid.

The precipitate is filtered off with suction, washed with water and is then dissolved in 150 ml of methylene chloride.

The dried (Na₂SO₄) solution is evaporated to a viscous liquid, which is triturated with 200 ml of diethylether-hexane (5:1), furnishing the pure title compound as nearly colourless crystals: m.p. 115°–116° C.

Example B

1[[(4-chloro-2-fluoro-5-isopropoxyphenyl)amino]carbonyl]-1,2,3,6-tetrahydro-2-pyridinecarboxylic acid-methyl ester (Compound 1.2)

To a stirred solution of 5,65 g (0,04 moles) of 1,2,3,6-tetrahydro-2-pyridinecarboxylic acid methyl ester in 75 ml of dry toluene are added dropwise without cooling 9,2 g (0,04 moles) of 4-chloro-2-fluoro-5-isopropoxyphenyl isocyanate, dissolved in 200 ml of dry toluene.

After the exothermic reaction (29°) has subsided, the reaction mixture is stirred 5 hours longer at ambient temperature and is then taken to dryness.

The residue is chromatographed on a silica gel column.

Elution with hexane-diethyl ether (3:2) affords the title compound, which is obtained initially as a yellowish syrup, but which subsequently solidifies, having a m.p. of 88°–89°.

Analogous to the procedures set forth in examples A and B, the compounds of Table 1 are obtained.

Example C 2-(4-chloro-2-fluoro-5-isopropoxyphenyl)-8,8a-dihydro-imidazo-[1,5-a]-pyridine-l,3(2H, 5H)-dione (Compound 2.3)

The solution of 1,43 g (0,004 moles) of 1[[(4-chloro-2-fluoro-5-isopropoxyphenyl)amino]carbonyl]-1,2,3,6-tetrahydro-2-pyridinecarboxylic acid in 20 ml of ethanol and 20 ml of 2N HCl is boiled under reflux for 4 hours. Rotevaporation of the reaction solution furnishes the title compound as a faintly yellow syrup, which is homogeneous by TLC (Rf=0,35 on silica gel with ethyl acetate-hexane 1:1) when visualized with a 1% KMnO₄ solution.

It solidifies completely to a crystalline mass on chilling overnight at −15°: m.p. 90°–92° (triturated with hexane).

Example D 2-(2,4-dichloro-5-isopropoxyphenyl)-8,8a-dihydro-imidazo[1,5-a]-pyridine-1,3(2H, 5H)-dione (Compound 2.1)

The suspension of 1,36 g (0,0035 moles) of 1[[(2,4-dichloro-5-isopropoxyphenyl)amino]carbonyl]-1,2,3,6-tetrahydro-2-pyridinecarboxylic acid-methyl ester in 18 ml of ethanol and 18 ml of 2N hydrochloric acid is refluxed for 4 hours and is then evaporated in vacuo.

The residue is taken up with methylene chloride, washed with 75 ml of rarer, dried (Na₂SO₄) and filtered.

The residual syrup left on evaporating the filtrate is dissolved in 20 ml of diethyl ether.

Chilling overnight at −18° affords the title compound as colourless crystals, having a m.p. of 125°–126°.

Example E 2-(4-chloro-2-fluoro-5-hydroxyphenyl)-8,8a-dihydro-imidazo[1,5-a]-pyridine-1,3-(2H,5H)-dione (Compound 2.2)

The mixture of 8,4 g (0,0217 moles) of 1[[(4-chloro-2-fluoro-5-methoxycarbonyloxyphenyl)amino ]carbonyl]-2pyridinecarboxylic acid-methyl ester, 3 g (0,0217 moles) of K₂CO₃ and 175 ml of methanol is stirred at 50° for two hours.

The resulting yellow reaction solution is then evaporated in vacuo and the residue treated with 200 ml of saturated NH₄Cl-solution.

The formed title compound is extracted into three 120 ml portions of diethyl ether and the ethereal extracts dried over anhydrous Na₂SO₄.

The crystalline mass left on rotevaporation of the solvent is triturated with hexane-diethylether (5:1), giving colourless crystals, m.p. 195°–197°.

Example F 2-(4-chloro-2-fluoro-5-isopropoxyphenyl)-8,8a-dihydro-imidazo [1,5-a]-pyridine-1,3(2H, 5H)-dione (Compound 2.3 )

To a stirred solution of 2,82 g (0.02 moles) of 1,2,3,6-tetrahydro-2-pyridinecarboxylic acid-methyl ester in 40 ml of dry toluene, which contains 0,8 ml of triethylamine, are added without cooling 4,6 g (0,02 moles) of 4-chloro-2-fluoro-5-isopropoxyphenyl isocyanate in 100 ml of dry toluene. When all the isocyanate has been introduced, the resulting reaction solution is stirred at room temperature for a period of 18 hours and is then evaporated in vacuo.

The remaining viscous liquid is dissolved in 50 ml of hexane-diethylether (1:1) and filtered.

The filtrate is kept overnight at −15° to give colourless crystals, having a m.p. of 90°–92°.

Following the procedure of Example F, the final compounds of Table 2 are prepared by the reaction of 1,2,3,6-tetrahydro-2pyridinecarboxylic acid-methyl ester with the corresponding arylisocyanates or arylisothiocyanates.

TABLE I

Urea Compounds of the formula I (A = NH)
PART A

| Example | $R_2$ | $R_3$ | $R_4$ | $R_6$ | $(R_5)m$ | m.p. or Rf on silica gel |
|---|---|---|---|---|---|---|
| 1.1 | F | Cl | $OC_3H_7$-i | COOH | H | 115–116° |
| 1.2 | F | Cl | $OC_3H_7$-1 | $COOCH_3$ | H | 88–89° |
| 1.3 | F | Cl | $OCOOCH_3$ | $COOCH_3$ | H | 109–111° |
| 1.4 | F | Cl | $OSO_2CH_3$ | $COOCH_3$ | H | 136–138° |
| 1.5 | Cl | Cl | $OC_3H_7$-i | $COOCH_3$ | H | 86–87° |
| 1.6 | H | Cl | H | COOH | H | 117–118° |
| 1.7 | F | Cl | Br | $COOCH_3$ | H | 103–105° |
| 1.8 | F | Cl | I | $COOCH_3$ | H | 112° |
| 1.9 | F | Cl | Cl | $COOCH_3$ | H | 118° |
| 1.10 | F | Cl | CN | $COOCH_3$ | H | 149–150° |
| 1.11 | F | Cl | $OCH_2C \equiv CH$ | $COOCH_3$ | H | 104–106° |
| 1.12 | F | Cl | $OC_3H_7$-n | $COOCH_3$ | H | 91° |
| 1.13 | F | Cl | $OCH_2CH_3$ | $COOCH_3$ | H | 63° |
| 1.14 | F | Cl | $OCH_3$ | $COOCH_3$ | H | 102° |
| 1.15 | F | Cl | O-cyclopentyl | $COOCH_3$ | H | 105° |
| 1.16 | F | Cl | $OCH_2CH=CHCH_3$ | $COOCH_3$ | H | |
| 1.17 | F | Cl | $OCH_2C(CH_3)=CH_2$ | $COOCH_3$ | H | |
| 1.18 | F | Cl | $OCH(CH_3)CH=CH_2$ | $COOCH_3$ | H | |
| 1.19 | F | Cl | $OCH_2CH=C(CH_3)_2$ | $COOCH_3$ | H | |
| 1.20 | F | Cl | $OCH_2C(Br)=CH_2$ | $COOCH_3$ | H | |
| 1.21 | F | Cl | $OCH_2CH=CH-Br$ | $COOCH_3$ | H | |
| 1.22 | F | Cl | $OCH_2CH=CH-COOCH_3$ | $COOCH_3$ | H | |
| 1.23 | F | Cl | $OC_3H_7$-i | $COOC_3H_7$-i | H | |
| 1.24 | F | Cl | $OC_3H_7$-i | $COOCH_2CH=CH_2$ | H | |
| 1.25 | F | Cl | $OC_3H_7$-i | $COOCH_2C \equiv CH$ | H | |
| 1.26 | F | Cl | $OC_3H_7$-i | $COOC(CH_3)HOCOCH_3$ | H | |
| 1.27 | F | Cl | $OC_3H_7$-i | $COOCH_2OCOCH_3$ | H | |
| 1.28 | F | Cl | $OC_3H_7$-i | $COON=C(CH_3)_2$ | H | |
| 1.29 | F | Cl | $OC_3H_7$-i | $CONHOCH_2COOCH_3$ | H | |
| 1.30 | F | Cl | $OC_3H_7$-i | $CONHSO_2$-phenyl | H | |
| 1.31 | F | Cl | $OC_3H_7$-i | $COSCH_2CH_3$ | H | |
| 1.32 | F | $CH_3$ | $OC_3H_7$-i | $COOCH_3$ | H | |
| 1.33 | F | CN | $OC_3H_7$-i | $COOCH_3$ | H | |
| 1.34 | F | CN | $COOC_4H_9$-s | $COOCH_3$ | H | |
| 1.35 | F | Cl | $CH_2SCH_3$ | $COOCH_3$ | H | |
| 1.36 | F | Cl | $CH_2SO_2CH_3$ | $COOCH_3$ | H | |
| 1.37 | F | Cl | $SO_2C_3H_7$-i | $COOCH_3$ | H | |
| 1.38 | F | Cl | $NO_2$ | $COOCH_3$ | H | 101° |
| 1.39 | F | Cl | $OC_3H_7$-i | $COOCH_2OCH_2CH_2OCH_3$ | H | |
| 1.40 | F | Cl | $OC_3H_7$-i | $COOCH_3$ | 2-$CH_3$ | |
| 1.41 | F | Cl | $OC_3H_7$-i | $COOCH_3$ | 6-$CH_3$ | |
| 1.42 | F | Cl | $OC_3H_7$-i | $COOCH_3$ | 4(5)-$CH_3$[1] | |
| 1.43 | F | Cl | $OC_3H_7$-i | $COOCH_3$ | 4(5)-$CH_2CH_3$[1] | |
| 1.44 | F | Cl | $OC_3H_7$-i | $COOCH_3$ | 4(5)Cl[1] | |
| 1.45 | F | Cl | $OC_3H_7$-i | $COOCH_3$ | 8-F | |
| 1.46 | F | Cl | $OC_3H_7$-i | $COOCH_3$ | 3,6-$(CH_3)_2$ | |
| 1.47 | F | Cl | $OC_3H_7$-i | $COOCH_3$ | 4,6,6-$(CH_3)_3$ | |
| 1.48 | F | Cl | $OC(CH_3)C \equiv CH$ | $COOCH_3$ | H | 103–105 |
| 1.49 | F | Cl | $OCH(CH_3)CH_2CH_3$ | $COOCH_3$ | H | 66° |
| 1.50 | F | Cl | $OCH_2$-phenyl | $COOCH_3$ | H | |
| 1.51 | F | Cl | $OCH(CH_3)$phenyl | $COOCH_3$ | H | |
| 1.52 | F | Cl | $OCH(CH_3)CH_2OCH_3$ | $COOCH_3$ | H | |
| 1.53 | F | Cl | $OCH_2C(O)CH_3$ | $COOCH_3$ | H | |
| 1.54 | F | Cl | $OCH_2CH=CH_2$ | $COOCH_3$ | H | |
| 1.55 | F | Cl | $OCH_2CH=CHCl$ | $COOCH_3$ | H | |
| 1.56 | F | Cl | $OCH_2CH(Cl)=CH_2$ | $COOCH_3$ | H | |
| 1.57 | F | Cl | $OCH_2$-(2,2-di-Cl-cyclopropyl) | $COOCH_3$ | H | |

TABLE I-continued

| Example | R₂ | R₃ | R₄ | R₆ | (R₅)ₘ | m.p. or Rf on silica gel |
|---|---|---|---|---|---|---|
| 1.58 | F | Cl | OCH₂(2-Cl-cyclopropyl) | COOCH₃ | H | |
| 1.59 | F | Cl | OCH₂-cyclopropyl | COOCH₃ | H | |
| 1.60 | F | Cl | OCH₂CH₂OCH₂CH₃ | COOCH₃ | H | |
| 1.61 | F | Cl | OCH₂-(tetrahydrofuran-2-yl) | COOCH₃ | H | |
| 1.62 | F | Cl | OCH₂-(tetrahydropyran-2-yl) | COOCH₃ | H | |
| 1.63 | F | Cl | OCH₂-(5,6-dihydro-2-H-thiin-3-yl) | COOCH₃ | H | |
| 1.64 | F | Cl | OCH₂-C(=NOCH₃)COOC₂H₅ | COOCH₃ | H | |
| 1.65 | F | Cl | OCH₂(1,3-dioxolan-2-yl) | COOCH₃ | H | |
| 1.66 | F | Cl | OCH₂-(1,3-dithiolan-2-yl) | COOCH₃ | H | |
| 1.67 | F | Cl | OCH₂—CO-(1,4-oxazin-4-yl) | COOCH₃ | H | |
| 1.68 | F | Cl | OCH₂COOC₅H₁₁-n | COOCH₃ | H | |
| 1.69 | F | Cl | O-(2-oxo-cyclopentyl-1) | COOCH₃ | H | |
| 1.70 | F | Cl | OP(O)(OCH₃)₂ | COOCH₃ | H | |
| 1.71 | F | Cl | OCH(SCH₃)—COOCH₂CH₂Cl | COOCH₃ | H | |
| 1.72 | F | Cl | OCH₂P(O)(OCH₂CH₃)₂ | COOCH₃ | H | |
| 1.73 | F | Cl | OCH₂CF₃ | COOCH₃ | H | |
| 1.74 | F | Cl | OCHF₂ | COOCH₃ | H | |
| 1.75 | F | Cl | OCH₂COOcyclopentyl | COOCH₃ | H | |
| 1.76 | F | Cl | OCH₂-(1-pyrazolyl) | COOCH₃ | H | |
| 1.77 | F | Cl | 4-[C₂H₅OOC—CH(CH₃)—O]phenoxy | COOCH₃ | H | |
| 1.78 | F | Cl | OCH₂-(thien-2-yl) | COOCH₃ | H | |
| 1.79 | F | Cl | OCH(CH₃)-(3-CH₃-1,2,4-oxadiazol-5-yl) | COOCH₃ | H | |
| 1.80 | F | Cl | SC₃H₇-i | COOCH₃ | H | 80–81° |
| 1.81 | F | Cl | SCH₂C≡CH | COOCH₃ | H | |
| 1.82 | F | Cl | SCH₂COOC₂H₅ | COOCH₃ | H | |
| 1.83 | F | Cl | SCH(CH₃)—COOC₂H₅ | COOCH₃ | H | |
| 1.84 | F | Cl | SCH₂-phenyl | COOCH₃ | H | |
| 1.85 | F | Cl | S-(tetrahydro-pyran-2-yl) | COOCH₃ | H | |
| 1.86 | F | Cl | NCH₂COOC₂H₅ | COOCH₃ | H | |
| 1.87 | F | Cl | N(CH₃)₂ | COOCH₃ | H | |
| 1.88 | F | Cl | N—(CH₃)—COOCH₂CH₃ | COOCH₃ | H | |
| 1.89 | F | Cl | NHCOCH(CH₃)—CH₂CH₃ | COOCH₃ | H | |
| 1.90 | F | Cl | NHCH(C₂H₅)—P(O)(C₂H₅)(OC₂H₅) | COOCH₃ | H | |
| 1.91 | F | Cl | COOC₃H₇-i | COOCH₃ | H | 0.43 (ethylacetate-hexane 1:1) |
| 1.92 | F | Cl | COOCH(CH₂F)₂ | COOCH₃ | H | |
| 1.93 | F | Cl | COOCH₂CH₂OCH₃ | COOCH₃ | H | |
| 1.94 | F | Cl | COON=C(CH₃)₂ | COOCH₃ | H | |
| 1.95 | F | Cl | COOCH₂F | COOCH₃ | H | |

| Example | R₂ | R₃ | R₄ | R₆ | (R₅)ₘ | m.p. or Rf on silica gel |
|---|---|---|---|---|---|---|
| 1.96 | F | Cl | COOCH₂CH₂OSi(CH₃)₃ | COOCH₃ | H | |
| 1.97 | F | Cl | COOCH₂Si(CH₃)₃ | COOCH₃ | H | |
| 1.98 | F | Cl | COOCH₂CH₂P(O)(OCH₃)₂ | COOCH₃ | H | |
| 1.99 | F | Cl | COOCH(CH₃)CH₂Si(CH₃)₃ | COOCH₃ | H | |
| 1.100 | F | Cl | COOCH(C₂H₅)P(O)(OCH₃)₂ | COOCH₃ | H | |
| 1.101 | F | Cl | COOCH₂COOC₂H₅ | COOCH₃ | H | |
| 1.102 | F | Cl | COOCH₂OCOCH₃ | COOCH₃ | H | |
| 1.103 | F | Cl | COOCH(CH₃)OCO-piperidin-1-yl | COOCH₃ | H | |
| 1.104 | F | Cl | CON(CH₃)₂ | COOCH₃ | H | |
| 1.105 | F | Cl | CON(CH₃)OCH₃ | COOCH₃ | H | |
| 1.106 | F | Cl | CONHSO₂CH₃ | COOCH₃ | H | |
| 1.107 | F | Cl | CONHOCH₂COOC₂H₅ | COOCH₃ | H | |

| Example | R₂ | R₃ | R₄ | R | (R₅)ₘ | m.p. or Rf on silica gel |
|---|---|---|---|---|---|---|
| 1.108 | F | Cl | CONHCH₂COOC₂H₅ | COOCH₃ | H | |
| 1.109 | F | Cl | CHO | COOCH₃ | H | |
| 1.110 | F | Cl | COOCH₃ | COOCH₃ | H | |
| 1.111 | F | Cl | 4-(C₂H₅OOC)-1,3-dioxolan-2-yl | COOCH₃ | H | |
| 1.112 | F | Cl | 2-CH₃-1,3-dioxolan-2-yl | COOCH₃ | H | |
| 1.113 | F | Cl | 4,4-di-CH₃-(4,5-dihydrooxazol-2-yl) | COOCH₃ | H | |
| 1.114 | F | Cl | CH₂CH(CH₃)₂ | COOCH₃ | H | |
| 1.116 | F | Cl | CH₂COOC₂H₅ | COOCH₃ | H | |
| 1.117 | F | Cl | CH₂C(CN)(CH₃)—COOC₂H₅ | COOCH₃ | H | |
| 1.118 | F | Cl | CH₂C—(CH₃)(COOC₂H₅)₂ | COOCH₃ | H | |
| 1.119 | F | Cl | CH₂OCH₃ | COOCH₃ | H | |
| 1.120 | F | Cl | CH₂OCH₂COOC₂H₅ | COOCH₃ | H | |

| Example | R₂ | R₃ | R₄ | R₆ | (R₅)ₘ | m.p. or Rf on silical gel |
|---|---|---|---|---|---|---|
| 1.121 | F | Cl | CH₂NHCH₂COOC₂H₅ | COOCH₃ | H | |
| 1.122 | F | Cl | CH₂CH₂CN | COOCH₃ | H | |
| 1.123 | F | Cl | CH₂CH₂COOC₂H₅ | COOCH₃ | H | |
| 1.124 | F | Cl | CH₂CH(CH₃)—COOC₂H₅ | COOCH₃ | H | |
| 1.125 | F | Cl | CH=CH—CN | COOCH₃ | H | |
| 1.126 | F | Cl | CH=CH—COOC₂H₅ | COOCH₃ | H | |
| 1.127 | F | Cl | CH=C(Br)—COOC₂H₅ | COOCH₃ | H | |
| 1.164 | F | Cl | COOCH₃ | COOCH₃ | H | 0.47 (ethylacetate:hexane 1:1) |
| 1.165 | F | Cl | CCl=CH₂ | COOCH₃ | H | 150–151° |
| 1.166 | F | Cl | C≡CH | COOCH₃ | H | 92–94° |

TABLE I-continued

Part B: Urea compounds of the formula Ar$^{(2)}$—NH—CO—N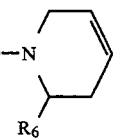

| Ex. No. | Ar$^{(2)}$ | R$_6$ | m.p. or Rf on silical gel |
|---|---|---|---|
| 1.128 | 5-F-indan-l-on-6-yl | COOCH$_3$ | 129°; 0,42 (ethylacetate) |
| 1.129 | 4-(C$_2$H$_5$OCOCH$_2$)-7-F—Ar$_1$$^{(3)}$ | COOCH$_3$ | 123–125° |
| 1.130 | (CH$_3$OCH$_2$)-7-F—Ar$_1$ | COOCH$_3$ | |
| 1.131 | 4-(CNCH$_2$)-7-F—Ar$_1$ | COOCH$_3$ | |
| 1.132 | 4-CH$_3$-7-F—Ar$_1$ | COOCH$_3$ | |
| 1.133 | 4-allyl-7-F—Ar$_1$ | COOCH$_3$ | |
| 1.134 | 4-CH$_2$-(tetrahydropyran-4-yl)-7-F—Ar$_1$ | COOCH$_3$ | |
| 1.135 | 4-CH$_2$-(5,6-dihydro-2H-thiin-3-yl)-7-F—Ar$_1$ | COOCH$_3$ | |
| 1.137 | 4-CH$_2$-(2-pyrazinyl)-7-F—Ar$_1$ | COOCH$_3$ | |

| Ex. No. | Ar | R$_6$ | m.p. or Rf on silica gel |
|---|---|---|---|
| 1.138 | 2,1,5-tri-F-benzo[d]-dioxole-6-yl | COOCH$_3$ | |
| 1.139 | 4-CH$_3$-7-F-benzo[e]-1,3-dioxine-6-yl | COOCH$_3$ | |
| 1.140 | 4-(2-propynyl)-7-F-benzo[b]-1,4-thiazin-3-on-6-yl | COOCH$_3$ | |
| 1.141 | 4-(2-propynyl)-7-F—Ar$_1$ | COOCH$_3$ | |
| 1.142 | 1-(2-propynyl)-6-F—Ar$_2$$^{(4)}$ | COOCH$_3$ | |
| 1.143 | 1-allyl-6-F—Ar$_2$ | COOCH$_3$ | |
| 1.144 | 1-(2-propynyl)-6-F—Ar$_3$$^{(5)}$ | COOCH$_3$ | |
| 1.145 | 1-allyl-6-F—Ar$_3$ | COOCH$_3$ | |
| 1.146 | 1-allyl-6-F-quinoline-2(1H)-on-7-yl | COOCH$_3$ | |
| 1.147 | 3-(2-propynyl)-6-F-benzo[d]-1,3-oxazole-2(3H)-on-5-yl | COOCH$_3$ | |
| 1.148 | 4-(1,2-oxazole-3-yl-CH$_2$)-7-F—Ar$_1$ | COOCH$_3$ | |
| 1.149 | 4-(5-CH$_3$-1,2,4-oxadiazol-3-yl-CH$_2$)-7-F—Ar$_1$ | COOCH$_3$ | |
| 1.150 | 3-(1,2-oxazole-3-yl-CH$_2$)-6-F—Ar$_4$$^{(6)}$ | COOCH$_3$ | |
| 1.151 | 3-(2-pyridyl-CH$_2$)-6-F—Ar$_4$ | COOCH$_3$ | |
| 1.152 | 5-F-2,3-dihydro-benzo[b]furan-6-yl | COOCH$_3$ | |
| 1.153 | 5-F-1-CH$_3$-indol-6-yl | COOCH$_3$ | |
| 1.154 | 1-(2-propynyl)-5-F-benzo[d]pyrazol-6-yl | COOCH$_3$ | |
| 1.155 | 1-(2-propynyl)-5-F-benzo[d]-1,2,3-triazol-6-yl | COOCH$_3$ | |
| 1.156 | 1-allyl-5-F-1,3-dihydro-indol-2-on-6-yl | COOCH$_3$ | |
| 1.157 | 5-F-1,3-dimethyl-1,3-dihydro-indol-2-on-6-yl | COOCH$_3$ | |
| 1.158 | 5-F-benzo[d]imidazol-2(1H,3H)-on-6-yl | COOCH$_3$ | |
| 1.159 | 5-F-1-(2-propynyl)-1H-indol-2,3-dion-6-yl | COOCH$_3$ | |
| 1.160 | 6-F-chroman-7-yl | COOCH$_3$ | |
| 1.161 | 6-F-2,3-dihydrobenzo[b]-1,4-dioxin-7-yl | COOCH$_3$ | |
| 1.162 | 6-F-1-(2-propynyl)-3,4-dihydroquinolin-2(1H)-on-7-yl | COOCH$_3$ | |
| 1.163 | 7-F-4-isopropyl-chromen-2-on-6-yl | COOCH$_3$ | |

TABLE 2

PART A

Hydantoin Compounds of the formula I (A and R$_6$ join together to form —N—C(X) so oriented such that N is tied to the C=O moiety of formula (I)

| Ex. No. | R$_2$ | R$_3$ | R$_4$ | X | (R$_5$)$_m$ | m.p. or Rf on silica gel |
|---|---|---|---|---|---|---|
| 2.1 | Cl | Cl | OC$_3$H$_7$-i | O | H | 125–126° |
| 2.2 | F | Cl | OH | O | H | 195–196° |
| 2.3 | F | Cl | OC$_3$H$_7$-i | O | H | 90–92° |
| 2.4 | F | Cl | OC$_3$H$_7$-i | S | H | 0,44 (hexane-ethyl acetate 1:1) |
| 2.5 | F | Cl | OCH$_3$ | O | H | 130–131° |
| 2.6 | F | Cl | OCH$_2$CN | O | H | 0,25 (hexane-ethyl acetate 1:2) |
| 2.7 | F | Cl | OCH(CH$_3$)COOCH$_3$ | O | H | 138–139° |
| 2.8 | F | Cl | Br | O | H | 115–116° |
| 2.9 | F | Cl | I | O | H | 135° |
| 2.10 | F | Cl | Cl | O | H | 116° |
| 2.11 | F | Cl | CN | O | H | 191° |
| 2.12 | F | Cl | OSO$_2$CH$_3$ | O | H | 143–144° |
| 2.13 | F | Cl | OCH$_2$C≡CH | O | H | 129–131° |
| 2.14 | F | Cl | OC$_3$H$_7$-n | O | H | 126° |
| 2.15 | F | Cl | OCH$_2$CH$_3$ | O | H | 127° |
| 2.16 | F | Cl | O-cyclopentyl | O | H | 113° |
| 2.17 | F | Cl | OCOOCH$_3$ | O | H | 117–118° |
| 2.18 | F | Cl | OCH$_2$CH=CHCH$_3$ | O | H | 90° |
| 2.19 | F | Cl | OCH(CH$_3$)CH=CH$_2$ | O | H | 0.4 (hexane-ethyl acetate 1:1) |
| 2.20 | F | Cl | OCH$_2$C(CH$_3$)=CH$_2$ | O | H | 127° |
| 2.21 | F | Cl | OCH$_2$CH=C(CH$_3$)$_2$ | O | H | |
| 2.22 | F | Cl | OCH$_2$C(Br)=CH$_2$ | O | H | 109–110° |
| 2.23 | F | Cl | OCH$_2$CH=CH—Br | O | H | 60–62° |
| 2.24 | F | Cl | OCH$_2$CH=CH—COOCH$_3$ | O | H | 135–136° |
| 2.25 | F | CN | OC$_3$H$_7$-i | O | H | 144° |
| 2.26 | F | CN | COOC$_4$H$_9$-sec | O | H | |

TABLE 2-continued

| Ex. | $R_2$ | $R_3$ | $R_4$ | X | $(R_5)_m$ | m.p. or Rf on silica gel |
|---|---|---|---|---|---|---|
| 2.27 | F | $CH_3$ | $OC_3H_7$-i | O | H | |
| 2.28 | F | Cl | $CH_2SCH_3$ | O | H | |
| 2.29 | F | Cl | $CH_2SO_2CH_3$ | O | H | |
| 2.30 | F | Cl | $SO_2C_3H_7$-i | O | H | 153° |
| 2.31 | F | Cl | $NO_2$ | O | H | 108° |
| 2.32 | F | Cl | $OC_3H_7$-i | O | 8a-$CH_3$ | |
| 2.33 | F | Cl | $OC_3H_7$-i | O | 5-$CH_3$ | |
| 2.34 | F | Cl | $OC_3H_7$-i | O | 6(7)-$CH_3$ | |
| 2.35 | F | Cl | $OC_3H_7$-i | O | 6(7)-$C_2H_5$ | |
| 2.36 | F | Cl | $OC_3H_7$-i | O | 6(7)-Cl | |
| 2.37 | F | Cl | $OC_3H_7$-i | O | 8-F | |
| 2.38 | F | Cl | $OC_3H_7$-i | O | 5,8-$(CH_3)_2$ | |
| 2.39 | F | Cl | $OC_3H_7$-i | O | 5,5,7-$(CH_3)_3$ | |
| 2.40 | F | Cl | $OCH(CH_3)-C\equiv CH$ | O | H | 0.32 (hexane-ethyl acetate 1:1) |
| 2.41 | F | Cl | $OCH(CH_3)-CH_2CH_3$ | O | H | 0.41 (hexane-diethylether 1:2) |
| 2.42 | F | Cl | $OCH_2$-phenyl | O | H | |
| 2.43 | F | Cl | $OCH(CH_3)$-phenyl | O | H | |
| 2.44 | F | Cl | $OC(CH_3)H-CH_2OCH_3$ | O | H | |
| 2.45 | F | Cl | $OCH_2C(O)CH_3$ | O | H | |
| 2.46 | F | Cl | $OCH_2CH=CH_2$ | O | H | 127° |
| 2.47 | F | Cl | $OCH_2CH=CHCl$ | O | H | 49–51° |
| 2.48 | F | Cl | $OCH_2CH(Cl)=CH_2$ | O | H | 101–102° |
| 2.49 | F | Cl | $OCH_2$-(2,2-diCl-cyclopropyl) | O | H | |
| 2.50 | F | Cl | $OCH_2$-(2,2-Cl-cylopropyl) | O | H | |
| 2.51 | F | Cl | $OCH_2$-cyclopropyl | O | H | |
| 2.52 | F | Cl | $OCH_2CH_2OCH_2CH_3$ | O | H | |
| 2.53 | F | Cl | $OCH_2$-(2-tetrahydrofuryl) | O | H | |
| 2.54 | F | Cl | $OCH_2$-(2-tetrahydropyranyl) | O | H | |
| 2.55 | F | Cl | $OCH_2$-(2H-5,6-dihydrothiin-3-yl) | O | H | |
| 2.56 | F | Cl | $OCH_2-C(=NOCH_3)-COOC_2H_5$ | O | H | |
| 2.57 | F | Cl | $OCH_2$-(1,3-dioxolan-2-yl) | O | H | |
| 2.58 | F | Cl | $OCH_2$-(1,3-dithiolan-2-yl) | O | H | |
| 2.59 | F | Cl | $OCH_2-CO$-(1,4-oxazin-4-yl) | O | H | |
| 2.60 | F | Cl | $OCH_2COOC_5H_{11}$-n | O | H | |
| 2.61 | F | Cl | O-(2-oxo-cyclopentyl) | O | H | |
| 2.62 | F | Cl | $OP(O)(OCH_3)_2$ | O | H | |
| 2.63 | F | Cl | $OCH(SCH_3)-COOCH_2CH_2Cl$ | O | H | |
| 2.64 | F | Cl | $OCH_2P(O)(OCH_2CH_3)_2$ | O | H | |
| 2.65 | F | Cl | $OCH_2CF_3$ | O | H | |
| 2.66 | F | Cl | $OCHF_2$ | O | H | |
| 2.67 | F | Cl | $OCH_2COO$(cyclopentyl) | O | H | |
| 2.68 | F | Cl | $OCH_2$-(1-pyrazolyl) | O | H | |
| 2.69 | F | Cl | 4-$[C_2H_3OOC-CH(CH_3)-O]$phenoxy | O | H | |
| 2.70 | F | Cl | $OCH_2$-(2-thienyl) | O | H | |
| 2.71 | F | Cl | $OCH(CH_3)$-(3-$CH_3$-1,2,4-oxadiazol-5-yl) | O | H | |
| 2.72 | F | Cl | $SC_3H_7$-i | O | H | 110–111° |
| 2.73 | F | Cl | $SCH_2C\equiv CH$ | O | H | |
| 2.74 | F | Cl | $SCH_2COOC_2H_5$ | O | H | |
| 2.75 | F | Cl | $SCH(CH_3)-COOC_2H_5$ | O | H | |
| 2.76 | F | Cl | $SCH_2$-phenyl | O | H | |
| 2.77 | F | Cl | S-(tetrahydro-2-pyranyl) | O | H | |
| 2.78 | F | Cl | $NCH_2COOC_2H_5$ | O | H | |
| 2.79 | F | Cl | $N(CH_3)_2$ | O | H | |
| 2.80 | F | Cl | $N-(CH_3)COOCH_2CH_3$ | O | H | |
| 2.81 | F | Cl | $NHCOCH(CH_3)-CH_2CH_3$ | O | H | |
| 2.82 | F | Cl | $NHCH(C_2H_5)-P(O)(C_2H_5)(OC_2H_5)$ | O | H | |
| 2.83 | F | Cl | $COOC_3H_7$-i | O | H | 0.38 (hexane-ethylacetate 1:1) |
| 2.84 | F | Cl | $COOCH(CH_2F)_2$ | O | H | |
| 2.85 | F | Cl | $COOCH_2CH_2OCH_3$ | O | H | |
| 2.86 | F | Cl | $COON=C(CH_3)_2$ | O | H | |
| 2.87 | F | Cl | $COOCH_2F$ | O | H | |
| 2.88 | F | Cl | $COOCH_2CH_2OSi(CH_3)_3$ | O | H | |
| 2.89 | F | Cl | $COOCH_2Si(CH_3)_3$ | O | H | |
| 2.90 | F | Cl | $COOCH_2CH_2P(O)(OCH_3)_2$ | O | H | |
| 2.91 | F | Cl | $COOCH(CH_3)CH_2Si(CH_3)_3$ | O | H | |
| 2.92 | F | Cl | $COOCH(C_2H_5)P(O)(OCH_3)_2$ | O | H | |
| 2.93 | F | Cl | $COOCH_2COOC_2H_5$ | O | H | |
| 2.94 | F | Cl | $COOCH_2OCOCH_3$ | O | H | |
| 2.95 | F | Cl | $COOCH(CH_3)OCO$-piperidin-1-yl | O | H | |
| 2.96 | F | Cl | $CON(CH_3)_2$ | O | H | |
| 2.97 | F | Cl | $CON(CH_3)(OCH_3)$ | O | H | |
| 2.98 | F | Cl | $CONHSO_2CH_3$ | O | H | |
| 2.99 | F | Cl | $CONHOCH_2COOC_2H_5$ | O | H | |
| 2.100 | F | Cl | $CONHCH_2COOC_2H_5$ | O | H | |
| 2.101 | F | Cl | CHO | O | H | |
| 2.102 | F | Cl | $COCH_3$ | O | H | |
| 2.103 | F | Cl | 4-$COOC_2H_5$-1,3-dioxolan-2-yl | O | H | |

TABLE 2-continued

| Ex. | | | | | | m.p. or Rf on silica gel |
|---|---|---|---|---|---|---|
| 2.104 | F | Cl | 2-CH$_3$-1,3-dioxolan-2-yl | O | H | |
| 2.106 | F | Cl | CH$_3$ | O | H | |
| 2.107 | F | Cl | CH$_2$CH(CH$_3$)$_2$ | O | H | |
| 2.108 | F | Cl | CH$_2$COOC$_2$H$_5$ | O | H | |
| 2.109 | F | Cl | CH$_2$C(CN)(CH$_3$)COOC$_2$H$_5$ | O | H | |
| 2.110 | F | Cl | CH$_2$C(CH$_3$)(COOC$_2$H$_5$)$_2$ | O | H | |
| 2.111 | F | Cl | CH$_2$OCH$_3$ | O | H | |
| 2.112 | F | Cl | CH$_2$OCH$_2$COOC$_2$H$_5$ | O | H | |
| 2.113 | F | Cl | CH$_2$NHCH$_2$COOC$_2$H$_5$ | O | H | |
| 2.114 | F | Cl | CH$_2$CH$_2$CN | O | H | |
| 2.115 | F | Cl | CH$_2$CH$_2$COOC$_2$H$_5$ | O | H | |
| 2.116 | F | Cl | CH$_2$CH(CH$_3$)—COOC$_2$H$_5$ | O | H | |
| 2.117 | F | Cl | CH=CH—CN | O | H | |
| 2.118 | F | Cl | CH=CH—COOC$_2$H$_5$ | O | H | |
| 2.119 | F | Cl | CH=C(Br)—COOC$_2$H$_5$ | O | H | |
| 2.156 | F | Cl | C≡CH | O | H | 133° |
| 2.157 | F | Cl | COOCH$_3$ | O | H | 158° |
| 2.158 | F | Cl | CCl=CH$_2$ | O | H | 0.29 (ethylacetate:hexane 1:1) |

PART B: Hydantoin compounds of the formula 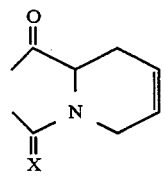

| Ex. | Ar$^{(2)}$ | X | m.p. or Rf on silica gel |
|---|---|---|---|
| 2.120 | 5-F-indan-1-on-6-yl | O | 198–199° |
| 2.121 | 4-(C$_2$H$_5$OOC—CH$_2$)-7-F—Ar$_1$ | O | 138–139° |
| 2.122 | 4-(CH$_3$OCH$_2$)-7-F—Ar$_1$ | O | |
| 2.123 | 4-(CNCH$_2$)-7-F—Ar$_1$ | O | |
| 1.124 | 4-CH$_3$-7-F—Ar$_1$ | O | |
| 1.125 | 4-allyl-7-F—Ar$_1$ | O | |
| 2.126 | 4-CH$_2$-(tetrahydropyran-4-yl)-7-F—Ar$_1$ | O | |
| 2.127 | 4-CH$_2$-(5,6-dihydro-2-6-thiin-3-yl) | O | |
| 2.128 | 4-CH$_2$-(2-pyridyl)-7-F—Ar$_1$ | O | |

| Ex. No. | Ar | X | m.p. or Rf on silica gel |
|---|---|---|---|
| 2.129 | 4-(pyrazin-2-yl-methyl)-7-F—Ar$_1$ | O | |
| 2.130 | 2,2,5-tri-F-benzo[d]-dioxole-6-yl | O | |
| 2.131 | 4-CH$_3$-7-F-benzo[e]-1,3-dioxine-6-yl | O | |
| 2.132 | 4-(2-propynyl)-7-F-benzo[b]-1,4-thiazin-3-on-6-yl | O | |
| 2.133 | 4-(2-propynyl)-7-F—Ar$_1$ | O | |
| 2.134 | 1-(2-propynyl)-6-F—Ar$_2$ | O | |
| 2.135 | 1-allyl-6-F—Ar$_2$ | O | |
| 2.136 | 1-(2-propynyl)-6-F—Ar$_3$ | O | |
| 2.137 | 1-allyl-6-F—Ar$_3$ | O | |
| 2.138 | 1-allyl-6-F-quinoline-2(1H)-on-7-yl | O | |
| 2.139 | 3-(2-propynyl)-6-F-benzo[d]-1,3-oxazole-2(3H)-on-5-yl | O | |
| 2.140 | 4-(1,2-oxazole-3-yl-CH$_2$)-7-F—Ar$_1$ | O | |
| 2.141 | 4-(5-CH$_3$-1,2,4-oxadiazol-3-yl-CH$_2$)-7-F—Ar$_1$ | O | |
| 2.142 | 3-(1,2-oxazole-3-yl-CH$_2$)-6-F—Ar$_4$ | O | |
| 2.143 | 3-(2-pyridyl-CH$_2$)-6-F—Ar$_4$ | O | |
| 2.144 | 5-F-2,3-dihydro-benzo[b]furan-6-yl | O | |
| 2.145 | 5-F-1-CH$_3$-indol-6-yl | O | |
| 2.146 | 1-(2-propynyl)-5-F-benzo[d]pyrazol-6-yl | O | |
| 2.147 | 1-(2-propynyl)-5-F-benzo[d]-1,2,3-triazol-6-yl | O | |
| 2.148 | 1-allyl-5-F-1,3-dihydro-indol-2-on-6-yl | O | |
| 2.149 | 5-F-1,3-dimethyl-1,3-dihydro-indol-2-on-6-yl | O | |
| 2.150 | 5-F-benzo[d]imidazol-2(1H,3H)-on-6yl | O | |
| 2.151 | 5-F-1-(2-propynyl)-1H-indol-2,3-dion-6-yl | O | |
| 2.152 | 6-F-chroman-7-yl | O | |
| 2.153 | 6-F-2,3-dihydrobenzo[b]-1,4-dioxin-7-yl | O | |
| 2.154 | 6-F-1-(2-propynyl)-3,4-dihydroquinolin-2(1H)-on-7-yl | O | |

TABLE 2-continued

| 2.155 | 7-F-4-isopropyl-chromen-2-on-6-yl | O |

Key to Abreviations
(1) isomeric mixture of 4- and 5-substituted compound
(2) Ar = 2-$R_2$-4-$R_3$-5-$R_4$-phenyl
(3) $Ar_1$ = 2,4-dihydro-benzo[b]-1,4-oxazin-3-on-6-yl
(4) $Ar_2$ = 3,4-dihydro-2H-quinoxalin-2-on-7yl
(5) $Ar_3$ = 1 H-quinoxalin-2-on-7-yl
(6) $Ar_4$ = Benzo[d]-1,3-thiazol-2(3H)-on-5-yl
(7) numbering convention

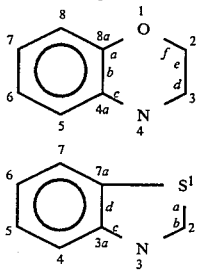

Biology

The herbicidal activity of the compounds of this application is demonstrated by experiments carried out for the pre-emergence and post-emergence control of a variety of weeds. Such weeds include *Abutilon theophrasti, Amaranthus retroflux, Sinapis alba, Solanum nigrum, Bromus tectorum, Setaria viridis, Avena fatua,* and *Echinochloa crus-galli.*

In pre-emergence testing, small plastic greenhouse pots filled with dry soil are seeded with the various weed seeds. Twenty-four hours or less after the seeding, the pots are sprayed with water until the soil is wet and the test compounds formulated as aqueous emulsions of acetone solutions containing emulsifiers are sprayed at the indicated concentrations emulsifiers are sprayed on the surface of the soil. After spraying, the soil containers are placed in the greenhouse and provided with supplementary heat as required and daily or more frequent watering. The plants are maintained under these conditions for a period of from 14 to 21 days, at which time the conditions of the plants and the degree of injury to the plants is rated.

In post-emergence testing, the compounds to be tested are formulated as aqueous emulsions and sprayed on the foliage of the various weed species that have attained a prescribed size. After spraying, the plants are placed in a greenhouse and watered daily or more frequently. Water is not applied to the foliage of the treated plants. The severity of the injury is determined 21 days after treatment and is rated.

In general, the compounds of this application demonstrate good activity against most of the weed varieties noted above. They are particularly active against *Abutilon theophrasti, Amaranthus retroflexus* and *Solanum nigrum,* in both pre- and post-emergence testing.

What is claimed is:

1. A compound of the formula (I)

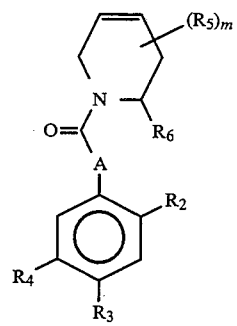

wherein
$R_2$ is halo;
$R_3$ is halo, cyano or $C_{1-4}$alkyl;
$R_4$ is H; halo; $NO_2$; $NH_2$; CN; OH; $C_{1-8}$alkyl optionally substituted by CN; $C_{2-8}$alkenyl optionally substituted by CN; $C_{2-5}$alkoxy carbonyl$C_{1-4}$alkyl, whereby the carbon atom of the alkyl group alpha to the alkoxycarbonyl group may be optionally substituted with one or more $C_{2-5}$alkoxycarbonyl group or a cyano group; $C_{2-5}$alkoxycarbonyl$C_{1-4}$alkoxy$C_{1-4}$alkyl; $C_{2-5}$alkoxycarbonyloxy; $C_{2-5}$alkoxycarbonyl$C_{2-5}$alkenyloxy; $C_{2-5}$alkynyloxy; $C_{3-6}$cycloalkyloxy; $C_{2-5}$alkenyloxy optionally substituted by halogen; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkoxy; $O(C_{1-4}$alkylene$)_nR_7$; $S(C_{1-4}$alkylene$)_nR_7$; $OCH(SR_8)COOR_9$; $NR_{10}R_{11}$; $COOR_{12}$; $C(O)NR_{13}R_{13}'$; $C(O)R_{14}$; $C_{1-5}$alkoxy optionally substituted by CN; $C_{2-5}$alkoxycarbonyl; $C_{1-4}$alkoxycarbonyl-$C_{1-4}$alkoxy or $C_{1-4}$alkylthio;
$R_5$ is hydrogen; $C_{1-4}$alkyl; halogen; or $C_{2-4}$alkenyl;
A and $R_6$ join together to form N—C(X) wherein X is O or S so oriented such that N is tied to the C=O moiety of formula (I);
$R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by O—$C_{1-4}$alkylene-$COOR_8$; $C_{2-5}$alkanoyl; $C_{2-5}$alkoxycarbonyl wherein the alkoxy is optionally substituted by $C_{1-4}$alkylthio; $C(O)NR_8R_{8'}$; $C(=NOR_{8'})COOR_{8'}$; or cyclopentoxycarbonyl;

$R_8$ and $R_{8'}$ independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl; $C_{2-5}$alkanoyl; $C_{2-5}$alkoxycarbonyl; or $C_{2-5}$alkoxycarbonyl$C_{1-4}$alkyl;

$R_{12}$ is $N=C_{2-8}$alkylidene; or $C_{1-4}$alkyl optionally substituted by one or more groups selected from halo, $C_{1-4}$alkoxy, $C_{2-5}$alkoxycarbonyl, $C_{2-5}$alkanoyloxy and di($C_{1-4}$alkyl)aminocarbonyloxy;

$R_{13}$ is H or $C_{1-4}$alkyl; and $R_{13'}$ is H, $C_{1-4}$alkyl, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy;

$R_{14}$ is H or $C_{1-4}$alkyl;

n is 0 or 1; and m is 0 to 4.

2. A compound of formula (I) according to claim 1 wherein A is N—C(O).

3. A compound of formula (I) according to claim 2 wherein $R_2$ is Cl or F, $R_3$ is Cl or CN and $R_5$ is H or halogen.

4. A compound of formula (I) according to claim 3 wherein $R_4$ is hydrogen; $C_{1-5}$alkoxy optionally substituted by CN; OH; $C_{1-4}$alkoxycarbonyl$C_{1-4}$alkoxy; halogen; CN; $C_{1-4}$alkylsulfonyloxy; $C_{2-5}$alkynyloxy; $C_{3-6}$cycloalkyloxy; $C_{2-5}$alkoxycarbonyloxy; $C_{2-5}$alkenyloxy optionally substituted by halogen; $C_{2-5}$alkoxycarbonyl; $C_{2-5}$alkenyloxy; $C_{1-4}$alkylsulfonyl; $NO_2$; $C_{1-4}$alkylthio; or $C_{2-5}$alkoxy-carbonyl.

5. A compound of formula (I) according to claim 4 wherein $R_2$ is F, $R_3$ is Cl and $R_4$ is $C_{1-4}$alkoxy, $C_{2-5}$alkynyloxy, $C_{2-5}$alkenyloxy or $C_{2-5}$alkoxycarbonyl.

6. A herbicidal composition comprising a compound of formula (I) as defined in claim 1 and an agriculturally acceptable carrier.

7. A method of combatting weeds which comprises applying to the weeds or their locus a herbicidally effective amount of the compound of formula (I) defined in claim 1.

8. A compound of the formula (I)

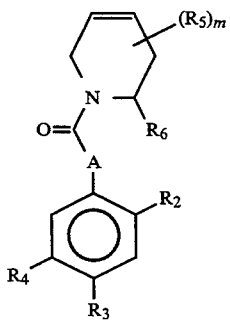

wherein $R_2$ is halo;

$R_3$ is halo, cyano or $C_{1-4}$alkyl;

$R_4$ is halo; $NO_2$; $NH_2$; CN; OH; $C_{1-8}$alkyl optionally substituted by CN; $C_{2-8}$alkenyl optionally substituted by CN; $C_{2-5}$alkoxy carbonyl$C_{1-4}$alkyl, whereby the carbon atom of the alkyl group alpha to the alkoxycarbonyl group may be optionally substituted with one or more $C_{2-5}$alkoxycarbonyl group or a cyano group;

$C_{2-5}$alkoxycarbonyl$C_{1-4}$alkoxy$C_{1-4}$alkyl; $C_{2-5}$alkoxycarbonyloxy; $C_{2-5}$alkoxycarbonyl$C_{2-5}$alkenyloxy; $C_{2-5}$alkynyloxy; $C_{3-6}$cycloalkyloxy; $C_{2-5}$alkenyloxy optionally substituted by halogen; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl; $C_{1-4}$alkylsulfonyloxy; $C_{1-4}$alkoxy$C_{1-4}$alkyl; $O(C_{1-4}$alkylene$)_nR_7$; $S(C_{1-4}$alkylene$)_nR_7$; $OCH(SR_8)COOR_9$; $NR_{10}R_{11}$; $COOR_{12}$; $C(O)NR_{13}R_{13'}$, $C(O)R_{14}$; $C_{1-5}$alkoxy optionally substituted by CN; $C_{2-5}$alkoxycarbonyl; $C_{1-4}$alkoxycarbonyl$C_{1-4}$alkoxy or $C_{1-4}$alkylthio;

$R_5$ is hydrogen; $C_{1-4}$alkyl; halogen; or $C_{2-4}$alkenyl;

A and $R_6$ join together to form N—C(X) wherein X is O or S so oriented such that N is tied to the C=O moiety of formula (I);

$R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by O—$C_{1-4}$alkylene-$COOR_8$; $C_{2-5}$alkanoyl; $C_{2-5}$alkoxycarbonyl wherein the alkoxy is optionally substituted by $C_{1-4}$alkylthio; $C(O)NR_8R_{8'}$; $C(=NOR_{8'})COOR_{8'}$; or cyclopentoxycarbonyl;

$R_8$ and $R_{8'}$, independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl; $C_{2-5}$alkanoyl; $C_{2-5}$alkoxycarbonyl; or $C_{2-5}$alkoxycarbonyl$C_{1-4}$alkyl;

$R_{12}$ is $N=C_{2-8}$alkylidene; or $C_{1-4}$alkyl optionally substituted by one or more groups selected from halo, $C_{1-4}$alkoxy, $C_{2-5}$alkoxycarbonyl, $C_{2-5}$alkanoyloxy, and di($C_{1-4}$alkyl)aminocarbonyloxy;

$R_{13}$ is H or $C_{1-4}$alkyl; and $R_{13'}$ is H, $C_{1-4}$alkyl, $C_{1-4}$alkoxy, phenyl, CHO, $C_{2-5}$alkanoyl, $C_4$alkylsulfonyl, $C_{2-5}$alkoxycarbonyl$C_{1-4}$alkyl or $C_{2-5}$alkoxycarbonyl$C_{1-4}$alkoxy;

$R_{14}$ is H or $C_{1-4}$alkyl;

n is 0 or 1; and m is 0 to 4.

9. A herbicidal composition comprising an herbicidally effective amount of a compound of the formula (I)

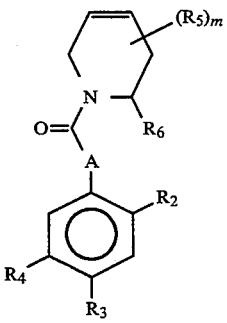

wherein $R_2$ is halo;

$R_3$ is halo, cyano or $C_{1-4}$alkyl;

$R_4$ is halo; $NO_2$; $NH_2$; CN; OH; $C_{1-8}$alkyl optionally substituted by CN; $C_{2-8}$alkenyl optionally substituted by CN; $C_{2-5}$alkoxy carbonyl$C_{1-4}$alkyl, whereby the carbon atom of the alkyl group alpha to the alkoxycarbonyl group may be optionally substituted with one or more $C_{2-5}$alkoxycarbonyl group or a cyano group; $C_{2-5}$alkoxycarbonyl$C_{1-4}$alkoxy$C_{1-4}$alkyl; $C_{2-5}$alkoxycarbonyloxy; $C_{2-5}$alkoxycarbonyl$C_{2-5}$alkenyloxy; $C_{2-5}$alkynyloxy; $C_{3-6}$cycloalkyloxy; $C_{2-5}$alkenyloxy optionally substituted by halogen; $C_{2-5}$alkoxycarbonyl$C_{2-5}$alkenyl, whereby the alkenyl group is optionally substituted by halogen; $C_{1-4}$alkylthio$C_{1-4}$alkyl; $C_{1-4}$alkylsulfonyl$C_{1-4}$alkyl; $C_{1-4}$alkylsulfonyl;. $C_{1-4}$alkylsulfonyloxy; $C_{1-4}$alkoxy$C_{1-4}$alkyl; $O(C_{1-4}alkylene)_nR_7$; $S(C_{1-4}alkylene)_nR_7$, $OCH(SR_8)COOR_9$; $NR_{10}R_{11}$; $COOR_{12}$; $C(O)NR_{13}R_{13'}$; $C(O)R_{14}$; $C_{1-5}$alkoxy optionally substituted by CN; $C_{2-5}$alkoxycarbonyl; $C_{1-4}$alkoxycarbonyl$C_{1-4}$alkoxy or $C_{1-4}$alkylthio;

$R_5$ is hydrogen; $C_{1-4}$alkyl; halogen; or $C_{2-4}$alkenyl;

A and $R_6$ join together to form N—C(X) wherein X is O or S so oriented such that N is tied to the C=O moiety of formula (I);

$R_7$ is H; $C_{1-4}$alkyl, $C_{2-5}$alkenyl, $C_{2-5}$alkynyl, or $C_{3-8}$cycloalkyl, which hydrocarbyl is unsubstituted or substituted by one or more halo or by CN; cyclopentanonyl; phenyl optionally substituted by O—$C_{1-4}$alkylene-$COOR_8$; $C_{2-5}$alkanoyl; $C_{2-5}$alkoxycarbonyl wherein the alkoxy is optionally substituted by $C_{1-4}$alkylthio; $C(O)NR_8R_{8'}$; $C(=NOR_8)COOR_{8'}$; or cyclopentoxycarbonyl;

$R_8$ and $R_{8'}$, independently are $C_{1-4}$alkyl;

$R_9$ is $C_{1-4}$alkyl optionally substituted by one or more halo;

$R_{10}$ is H or $C_{1-4}$alkyl;

$R_{11}$ is H; $C_{1-4}$alkyl; $C_{2-5}$alkanoyl; $C_{2-5}$alkoxycarbonyl; or $C_{2-5}$alkoxycarbonyl$C_{1-4}$alkyl;

$R_{12}$ is N=$C_{2-8}$alkylidene; or $C_{1-4}$alkyl optionally substituted by one or more groups selected from halo, $C_{1-4}$alkoxy, $C_{2-5}$alkanoyloxy, and di($C_{1-4}$alkyl)aminocarbonyloxy;

$R_{13}$ is H or $C_{1-4}$alkyl; and $R_{13'}$ is H, $C_{1-4}$alkyl, $C_{1-4}$alkoxy, phenyl, CHO, $C_{2-5}$alkanoyl, $C_{1-4}$alkylsulfonyl, $C_{2-5}$alkoxycarbonyl$C_{1-4}$alkyl or $C_{2-5}$alkoxycarbonyl$C_{1-4}$alkoxy;

$R_{14}$ is H or $C_{1-4}$alkyl;

n is 0 or 1;

m is 0 to 4; and an agriculturally acceptable carrier.

10. A herbicidal composition according to claim 9 wherein A is N—C(O).

11. A herbicidal composition according to claim 10 wherein $R_2$ is Cl or F, $R_3$ is Cl or CN and $R_5$ is H or halogen.

12. A herbicidal composition according to claim 11 wherein $R_4$ is $C_{1-5}$alkoxy optionally substituted by CN; OH; $C_{1-4}$alkoxycarbonyl$C_{1-4}$alkoxy; halogen; CN; $C_{1-4}$alkylsulfonyloxy; $C_{2-5}$alkynyloxy; $C_{3-6}$cycloalkyloxy; $C_{2-5}$alkoxycarbonyloxy; $C_{2-5}$alkenyloxy optionally substituted by halogen; $C_{2-5}$alkoxycarbonyl; $C_{2-5}$alkenyloxy; $C_{1-4}$alkylsulfonyl; $NO_2$; or $C_{1-4}$alkylthio.

13. A herbicidal composition according to claim 12 wherein $R_2$ is F; $R_3$ is Cl and $R_4$ is $C_{1-4}$alkoxy, $C_{2-5}$alkynyloxy, $C_{2-5}$alkenyloxy or $C_2$-$C_5$alkoxycarbonyl.

14. A method of combatting weeds which comprises applying to the weeds or their locus a herbicidally effective amount of the compound of formula (I) defined in claim 9.

* * * * *